(12) United States Patent
Ash et al.

(10) Patent No.: US 9,817,946 B2
(45) Date of Patent: Nov. 14, 2017

(54) GRAPHIC REPRESENTATIONS OF HEALTH-RELATED STATUS

(75) Inventors: Michael A Ash, Parkville, MO (US); Todd Jeffrey Reynolds, Kansas City, MO (US); Harlen Hays, Lawrence, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 978 days.

(21) Appl. No.: 13/328,647

(22) Filed: Dec. 16, 2011

(65) Prior Publication Data
US 2013/0158968 A1    Jun. 20, 2013

(51) Int. Cl.
G06K 9/00       (2006.01)
G06G 7/60       (2006.01)
G06F 19/00      (2011.01)

(52) U.S. Cl.
CPC ........ *G06F 19/3406* (2013.01); *G06F 19/345* (2013.01); *G06F 19/3431* (2013.01)

(58) Field of Classification Search
CPC ............. G06F 19/3437; G06F 19/3406; G06F 19/345; A61B 2019/505; A61B 3/10
USPC ............................................. 705/2
See application file for complete search history.

(56) References Cited

U.S. PATENT DOCUMENTS

| | | | |
|---|---|---|---|
| 2008/0077019 A1* | 3/2008 | Xiao ................. | A61B 5/01 600/474 |
| 2010/0324420 A1* | 12/2010 | Snook et al. ................. | 600/443 |
| 2011/0129130 A1* | 6/2011 | Avinash ............ | G06F 19/3443 382/128 |
| 2013/0060300 A1* | 3/2013 | Polefko ............. | A61N 1/36017 607/46 |

* cited by examiner

*Primary Examiner* — Hiep V Nguyen
(74) *Attorney, Agent, or Firm* — Shook, Hardy & Bacon L.L.P.

(57) ABSTRACT

Methods, computer systems, and computer-readable storage media for generating graphical representations of health-related variables are provided. The graphical representations include a first body-image representation of a user at a current period of time. The graphical representations also include a second body-image representation that represents the user at a future period of time, the user in a simulated clinical "what-if" scenario, or members of the population-at-large that share similar demographic traits with the user.

20 Claims, 7 Drawing Sheets

GRAPHIC REPRESENTATIONS OF HEALTH-RELATED STATUS

BACKGROUND

With the complexity and volume of health-related information in today's modern world, healthcare consumers often struggle with comprehending how this information influences their lives. A statistic such as "One in ten people will develop complications from smoking" has little effect on the typical healthcare consumer because it lacks any type of visceral, personal impact. As well, younger healthcare consumers who are in reasonably good shape because of their age have little idea how their current lifestyle decisions or health conditions will impact their lives, both physically and mentally, in the future.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Embodiments of the present invention are directed to methods, computer systems, and computer-readable storage media for generating and displaying graphical representations of health-related variables. In brief and at a high level, the present embodiments are designed to display health-related information to a user in a manner that is personal to the user and provides a strong visual impact. A body-image representation of the user may be utilized to visually represent a number of health-related variables associated with the user. The user is able to interact with the variables and see the impact of the variables on, for example, a body-image representation of the user at a future point in time. Other examples include comparing the body-image representation of the user with a body-image representation that characterizes members of the population-at-large that share similar demographic traits with the user. The user may also be able to simulate clinical "what-if" scenarios. For instance, the user may be able to view a body-image representation of the user if the user was suffering from depression, end-stage diabetes mellitus, or congestive heart failure. The result is a unique and personal way to educate healthcare consumers about the impact their choices have on lifestyle, health, and physical appearance.

BRIEF DESCRIPTION OF THE DRAWINGS

Embodiments are described in detail below with reference to the attached drawing figures, wherein.

DETAILED DESCRIPTION

Figure 1:
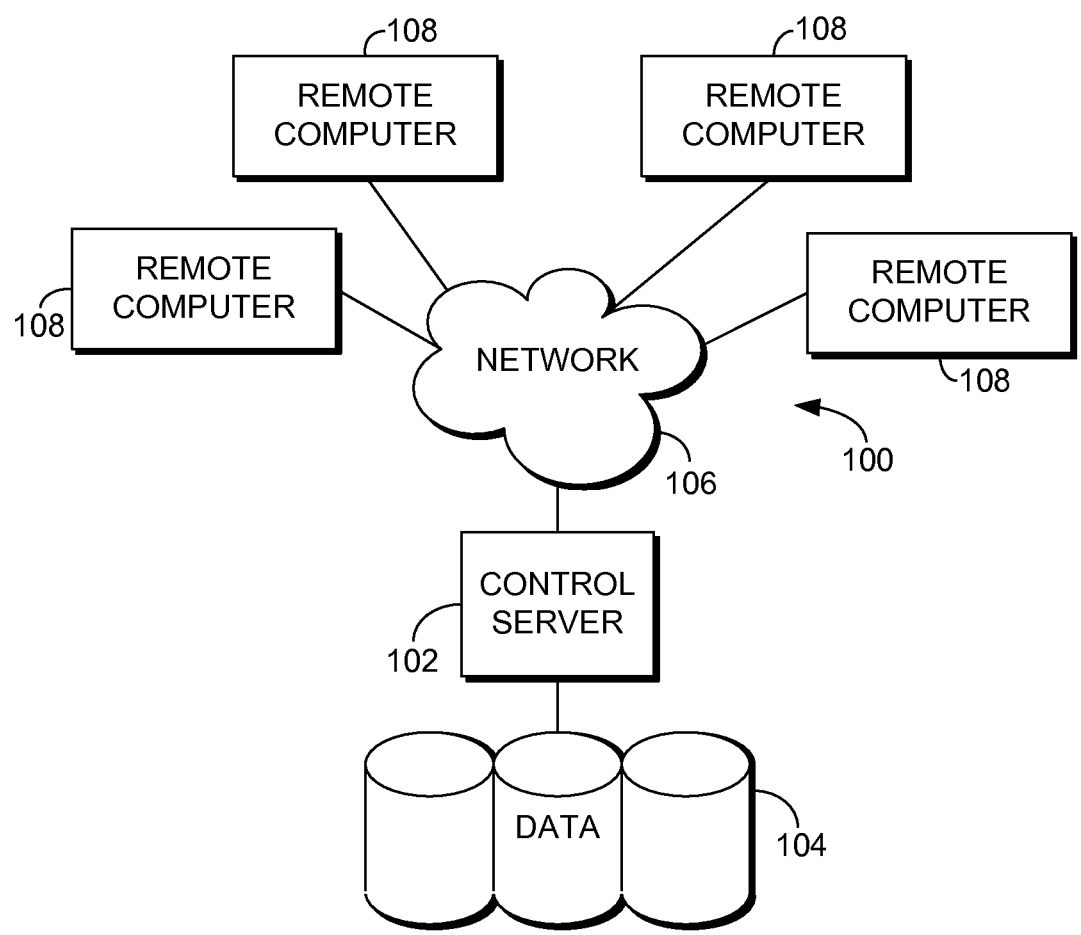
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, computer systems, and computer-readable storage media for generating and displaying graphical representations of health-related variables. Embodiments are designed to display health-related information to a user in a manner that is personal to the user and provides a strong visual impact. A body-image representation of the user may be utilized to visually represent a number of health-related variables associated with the user. The user is able to interact with the variables and see the impact of the variables on, for example, a body-image representation of the user at a future point in time. Other examples include comparing the body-image representation of the user with a body-image representation that characterizes members of the population-at-large that share similar demographic traits with the user. The user may also be able to simulate clinical "what-if" scenarios. For instance, the user may be able to view a body-image representation of the user if the user was suffering from depression, end-stage diabetes mellitus, or congestive heart failure. The result is a unique and personal way to educate healthcare consumers about the impact their choices have on lifestyle, health, and physical appearance.

Accordingly, in one embodiment, the present invention is directed to one or more computer-readable storage media, executable by a computing device, to display a graphical user interface (GUI) for displaying health-related variables in the form of body-image representations. The GUI comprises a first body-image representation of a user; the first body-image representation comprises a graphical representation of health-related variables associated with the user at a current period of time. The GUI also comprises a second body-image representation of the user; the second body-image representation is in the same viewable area as the first body-image representation and comprises a graphical representation of health-related variables associated with at least one of: 1) the user at a future period of time; 2) the user with a simulated medical condition; or 3) members of the population-at-large.

In another embodiment, the present invention is directed to one or more computer-readable storage media, executable by a computing device, to display a graphical user interface (GUI) for displaying graphical representations of health-related variables. The GUI comprises a first body-image representation; the first body-image representation comprising a graphical representation of health-related variables associated with a user at a current period of time. The GUI also comprises a second body-image representation that adaptively alters in visual appearance in response to a selection by the user of at least one health-related variables of a set of health-related variables. The second body-image representation is in the same viewable area as the first body-image representation.

In yet another embodiment, the present invention is directed to one or more computer-readable storage media, executable by a computing device, to display a graphical user interface (GUI) for displaying graphical representations of health-related variables. The GUI comprises a first display area configured to display a first body-image representation of a user; the first body-image representation comprises a graphical representation of health-related variables associated with the user at a current period of time. The GUI also comprises a second display area configured to display at least a portion of a set of health-related variables; the second display area is in the same viewable area as the first display area, and the at least a portion of the set of health-related variables has a selectable option with which it is associated.

Continuing, the GUI also comprises a third display area configured to display a second body-image representation of a user. The third display area is in the same viewable area as the first and second display area, and the third display area comprises a graphical representation of health-related variables associated with at least one of: 1) the user at a future point in time; 2) members of the population-at-large; or 3) the user after the user selects one of the health-related variables associated with the second display area. Additionally, the GUI comprises a fourth display area configured to display one or more health scores associated with the user; the fourth display area is in the same viewable area as the first, second, and third display areas.

Having briefly described embodiments of the present invention, an exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
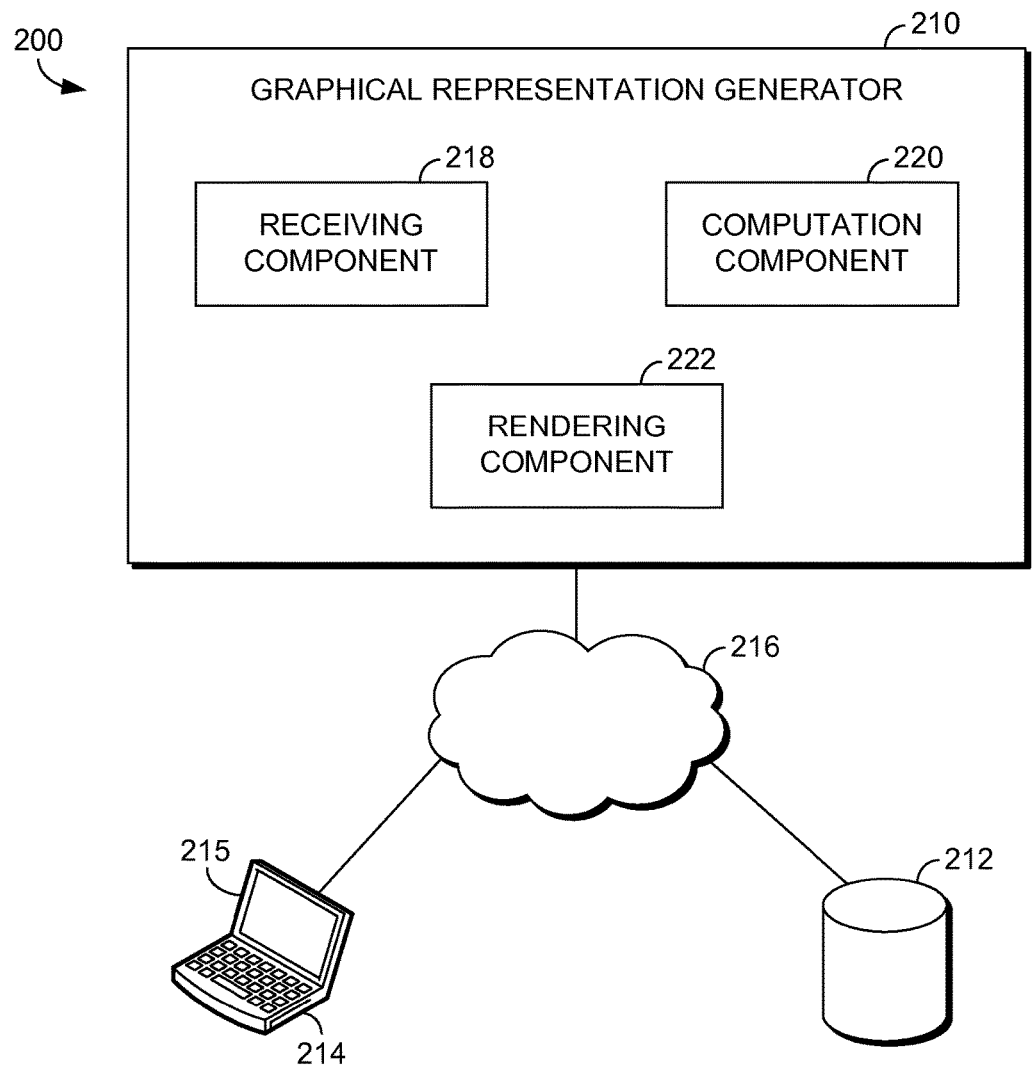
FIG. 2 is a block diagram of an exemplary computing system environment suitable for generating a graphical representation of health-related variables.

Turning now to FIG. 2, an exemplary computing system environment 200 is depicted. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes a graphical representation generator 210, a data store 212, and an end-user computing device 214 with a display screen 215 all in communication with one another via a network 216.

The network 216 may include, without limitation, one or more local area networks (LANs) and/or wide area networks (WANs). Such networking environments are commonplace in offices, enterprise-wide computer networks, intranets and the Internet. Accordingly, the network 216 is not further described herein.

In some embodiments, one or more of the illustrated components/modules may be implemented as stand-alone applications. In other embodiments, one or more of the illustrated components/modules may be integrated directly into the operating system of the graphical representation generator 210. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the graphical representation generator 210 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 212 is configured to store information for use by, for example, the graphical representation generator 210. The information stored in association with the data store 212 is configured to be searchable for one or more of the items of information stored in association therewith. The information stored in association with the data store 212 may comprise general information about health-related variables used by the graphical representation generator 210. As used throughout this application, the term "health-related variables" means any piece of health-related information. This may include everything from patient identifying information to exercise habits to a specific lab value. As such, it is meant to be a broad definition that encompasses the many pieces of information used in healthcare and related to a person's health.

The data store 212 may store information concerning personal health risk assessments completed by users, results from biometric screenings of users, and health-related insurance claims. A personal health risk assessment is a questionnaire that gathers information concerning the user's health history (both physical and mental) and lifestyle; it is completed by the user. Biometric screenings are screening tests and procedures designed to capture general health information. Information from biometric screenings may include information related to height, weight, blood pressure, as well as general lab results that measure glucose levels, cholesterol levels, thyroid levels, and the like. Health-related insurance claims provide information such as number of hospital visits including emergency room visits, reasons for visits, costs associated with care, and the like.

The data store 212 may also comprise an electronic medical record (EMR). In turn, the EMR may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

As well, the data store 212 may store information concerning decision-support algorithms, reference materials, recommendation protocols, and the like. These materials may be used by the graphical representation generator 210 to determine, for example, the importance of any one health-related variable and/or the interplay between different health-related variables. The data store 212 may also store health-related information associated with the population-at-large. This may include health-related variables associated with a particular demographic group.

The content and volume of such information in the data store 212 are not intended to limit the scope of embodiments of the present invention in any way. Further, though illustrated as a single, independent component, the data store 212 may, in fact, be a plurality of storage devices, for instance, a database cluster, portions of which may reside on the graphical representation generator 210, the end-user computing device 214, and/or any combination thereof.

As shown, the end-user computing device 214 includes a display screen 215. The display screen 215 is configured to display information to the user of the end-user computing device 214, for instance, information relevant to communications initiated by and/or received by the end-user computing device 214, information concerning graphical representations of health-related variables, and/or the like. Embodiments are not intended to be limited to visual display but rather may also include audio presentation, combined audio/visual presentation, and the like. The end-user computing device 214 may be any type of display device suitable for presenting a graphical user interface. Such computing devices may include, without limitation, a computer, such as, for example, any of the remote computers 108 described above with reference to FIG. 1. Other types of display devices may include tablet PCs, PDAs, mobile phones, smart phones, as well as conventional display devices such as televisions.

Components of the graphical representation generator 210 may include a processing unit, internal system memory, and a suitable system bus for coupling various system components, including one or more data stores for storing information (e.g., files and metadata associated therewith). The graphical representation generator 210 typically includes, or has access to, a variety of computer-readable media.

The computing system environment 200 is merely exemplary. While the graphical representation generator 210 is illustrated as a single unit, it will be appreciated that the graphical representation generator 210 is scalable. For example, the graphical representation generator 210 may in actuality include a plurality of computing devices in communication with one another. Moreover, the data store 212, or portions thereof, may be included within, for instance, the graphical representation generator 210 as a computer-storage medium. The single unit depictions are meant for clarity, not to limit the scope of embodiments in any form.

As shown in FIG. 2, the graphical representation generator 210 comprises a receiving component 218, a computation component 220, and a rendering component 222. In some embodiments, one or more of the components 218, 220, and 222 may be implemented as stand-alone applications. In other embodiments, one or more of the components 218, 220, and 222 may be integrated directly into the operating system of, for example, any of the remote computers 108 or the control server 102 of FIG. 1, or the end-user computing device 214 of FIG. 2. The components 218, 220, and 222 illustrated in FIG. 2 are exemplary in nature and in number and should not be construed as limiting. Any number of components may be employed to achieve the desired functionality within the scope of embodiments hereof.

The receiving component 218 is configured to receive one or more user requests, inputs, and/or selections. For the purposes of this application, a user may be defined as any person or party interested in viewing healthcare information in a graphical form. Thus, the user may be, for instance, a patient under the care of a clinician or a general healthcare consumer. As well, the user may be a clinician who cares for any number of patients. The receiving component 218 may receive requests for graphical representations of health-related variables. The receiving component 218 is also configured to receive user selections. The user selections may be selections of answers on a personal health assessment, selections associated with the graphical representations of health-related variables, selections of customization variables, and the like. This process will be explained in greater depth below. Further, the receiving component 218 is configured to receive user inputs in the form of numerical inputs or textual inputs. For example, a user may input a weight, or possibly a blood glucose level if the user is a diabetic. As well, a clinician caring for a patient may input results from biometric screening tests, or results and/or notes from a recent patient encounter with the patient.

The computation component 220 is configured to generate one or more health scores associated with a user. A health score is a percentile score bounded between 0 and 100 and gives an indication of the user's overall health or the user's health with respect to one or more discrete health-related variables as compared to members of the population-at-large or subsets of the population-at-large. In one aspect, the computation component 220 uses principal component analysis (PCA) to generate the one or more health scores. In brief and at a high level, PCA is a statistical technique that generates a finite set of components or factors from an initial set of correlated variables. Each factor is a rotated linear weighted combination of the initial set of correlated variables. With respect to the present application, the factors have been rotated via the oblique varimax methodology allowing for one variable to load on multiple factors. The initial set of correlated variables may comprise health-related variables drawn from personal health risk assessments, biometric screenings, health-related insurance claims, an electronic medical record, inputted values, and the like. PCA is a data reduction technique utilized to consolidate the statistical predictive power contained within these data sources while maintaining the complex nature of individual health.

The number of factors derived from the initial set of correlated variables may be restricted in number such that only meaningful amounts of variance are accounted for. In one aspect, each factor may encompass a different number of variables, with the number of variables associated with any one factor being dependent upon the degree of correlation between the variables—highly-correlated variables are likely to be associated with the same factor. In another aspect, each factor may encompass the same number of variables, but a variable may be weighted differently within each factor. Factors may encompass variables related to, for example, overall health, mental health, acute health, injury risk, chronic disease risk, and the like.

Next, the computation component 220 generates a health score for each factor that indicates where the user stands with respect to the retained factors. Again, this is accomplished by using the principles of PCA. The health score (otherwise known as a factor score or component score in PCA) is a linear composite of the optimally-weighted health-related variables. A health score may be generated for each one of the retained factors by converting the Z-score created by each factor calculation into a percentile rank. The Z-score follows a normal distribution with mean equal to zero. This is accomplished through look-up table conversions of the Z-score. Thus, each factor can be interpreted as measuring a different facet of health such as an overall health score, a mental health score, an acute health score, an injury risk health score, a chronic disease risk health score, and the like. Each variable (i.e., Body Mass Index) can contribute to multiple different health scores.

Figure 7:
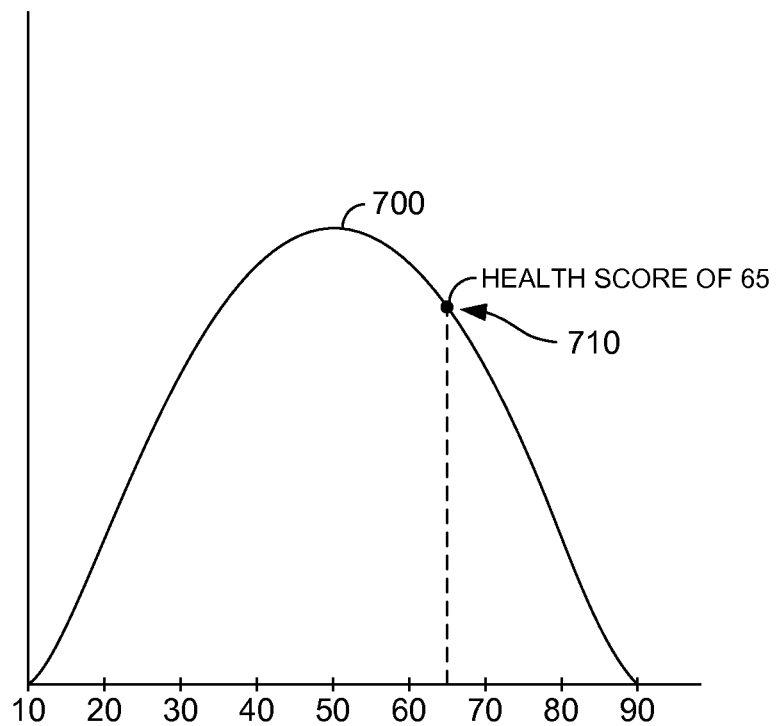
FIG. 7 depicts an exemplary bell-shaped curve and a generated health score in accordance with an embodiment of the present invention.

As mentioned above, the health score is a percentile bounded between 0 and 100 and gives an indication of where the user stands with respect to any one factor as compared to members of the population-at-large. This is graphically shown in FIG. 7 which depicts a bell-shaped curve 700 with a Gaussian distribution corresponding to a particular factor (for example, a mental health factor). Utilizing the Z-score calculated for the factor deemed to represent mental health, a Z-score of approximately 0.35 would be converted to an overall mental health score of 65 for a user (shown at element 710), indicating that the user has a mental health score that is better than 65% of the population.

When a user is compared to a subset of the population-at-large, further calibration is needed to give an accurate portrayal of the user's health status in relation to others within the subset. For example, the same Z-score calculated for mental health can also be used to create a percentile rank limited to one gender. This further step requires calibrating the percentile rank to be among only individuals of one gender. This is done by creating a normal distribution of the Z-score among the gender of interest and then converting the new position within the bell curve to a percentile rank. Thus, it is possible for an individual to have a mental health score in the $65^{th}$ percentile when compared to the population-at-large but to have a mental health score in the $80^{th}$ percentile when compared to individuals who are the same gender as the user.

The rendering component 222 of FIG. 2 is configured to render for display one or more graphical representations of health-related variables stored in, for example, the data store 212. The graphical representations may be in the form of score cards, gauges, graphs, icons, pictorial representations, and the like. In one aspect, the rendering component 222 utilizes decision-support algorithms, evidence-based protocols, and/or reference materials (stored in, for example, the data store 212) to determine which health-related variables to graphically represent. For example, a lab result in the user's EMR may indicate a non-fasting elevated blood glucose level. However, a decision-support algorithm for Diabetes Mellitus Type I indicates that a fasting blood glucose level is necessary to diagnose this condition. Based on this, the rendering component 222 may not display any graphical representations dealing with Diabetes Mellitus Type I. Instead of displaying a graphical representation of Diabetes Mellitus Type I, the rendering component 222 may display a notification to the user that a fasting blood glucose level should be obtained.

In another aspect, the user is able to select which health-related variables are graphically represented by the rendering component 222. This helps to make the graphical representation personal to the user. For example, the user may select certain health-related variables in which the user is interested. The user selections are received by the receiving component 222 and subsequently used by the rendering component 222 to render a graphical representation of the selected variables. The visual appearance as well as the information provided by the graphical representations may evolve over time as more health-related variables are added to the data store 212. In yet another aspect, the rendering component 222 utilizes a combination of user selections of health-related variables and determinations based on decision-support algorithms to render a graphical representation of health-related variables. Any and all such combinations are within the scope of embodiments of the present invention.

The graphical representations can encompass multiple health-related variables at any one time. For example, a single graphical representation could encompass health-related variables related to diabetes mellitus and congestive heart failure. Further, the graphical representations are designed to illustrate the interplay between the different health-related variables. It is a rare situation that a user is afflicted with only a single disease condition or healthcare concern. In reality, patients that suffer from one condition often suffer from other conditions. These different health conditions often interact with each other and with lifestyle choices to produce an overall health picture for the patient. The rendering component 222 is configured to take into account the interplay between different health-related variables when generating the graphical representations.

In one aspect of the invention, the graphical representation of health-related variables is in the form of a body-image representation. The body-image representation may be an outline of a generally male-looking body or a generally female-looking body in various different poses. The body-image representation may also be an anatomically correct, iconic representation of the user. With respect to this aspect, the user is able to customize the visual appearance of the body-image representation by selecting one or more characteristics (the selections are received by, for example, the receiving component 218). The selected characteristics may include gender, a body habitus, race, facial characteristics, hair color, and the like. The user may also be able to customize the face of the iconic representation using a picture of the user. The body-image representation may be one-dimensional or three-dimensional in nature. For example, the body-image representation may comprise a three-dimensional structure that rotates to show the front and back of the structure.

The body-image representation may, in one aspect, be outlined with a color to indicate a health problem that affects multiple organs and/or systems. Distinct disease conditions could be color-coded with distinct colors. For example, a teal outline could represent the disease condition of diabetes mellitus. Instead of outlining the body-image representation with a colored line, a colored halo could be used instead.

The rendering component 222 is also configured to render visual indicators on the body-image representation that represent areas of concern for the user. The visual indicators may be displayed over an anatomical position that corresponds to an affected organ or system. The visual indicators may be in the form of a dot, a stylized version of the affected organ and/or system, or an anatomically correct representation of the affected organ and/or system. Further, the visual indicators may be color-coded or shaped differently to indicate a status of the affected organ and/or system. By way of illustrative example, and not by limitation, the visual indicators may be color-coded red to indicate "critical," dark grey for "currently managing," orange for "needs attention," and light grey for "at risk."

The rendering component 222 is further configured to render a first body-image representation that comprises a graphical representation of health-related variables at a current time period and a second body-image representation that comprises a graphical representation of health-related variables at a future time period; the future time period may be, for example, five to ten years in the future. In this case, actual values of health-related variables are used to generate the first body-image representation at the current time period, and predicted or expected values of health-related variables are used to generate the second body-image representation at the future time period. The user is able to view the first and second body-image representations side-by-side to see the impact of time on the body as a whole, or upon an organ and/or system in particular.

The rendering component 222 is also configured to render a first body-image representation of a user at a current period of time and a second body-image representation that represents members of the population-at-large that share similar demographic traits with the user. The first body-image representation is generated from actual values of health-related variables associated with the user. The second body-image representation is generated from composite values of health-related variables associated with members of the population-at-large that share similar demographic traits with the user. The shared demographic traits may include, for example, age, gender, race, or any combination thereof.

Additionally, the rendering component 222 is configured to render a first body-image representation of a user at a current period of time and a second body-image representation that represents the user in a variety of clinical "what-if" scenarios. For example, the user may select a clinical "what-if" scenario and see the predicted results displayed on the second body-image representation. Some illustrative clinical "what-if" scenarios include starting a medication, losing weight, starting to exercise, choosing a cheaper medication, decreasing or ceasing smoking, increasing alcohol intake, and the like. As mentioned above, there may be interplay between the health-related variables. For instance, the clinical "what-if" scenario of starting to exercise might not only influence weight loss, but it may also positively influence a user's mental health, which, in turn, can positively influence certain disease conditions. All of these interactions can be graphically displayed on the second body-image representation. The first body-image representation is generated using actual values of health-related variables associated with the user, while the second body-image representation is generated using predicted or expected values of health-related variables associated with the user.

Figure 3:
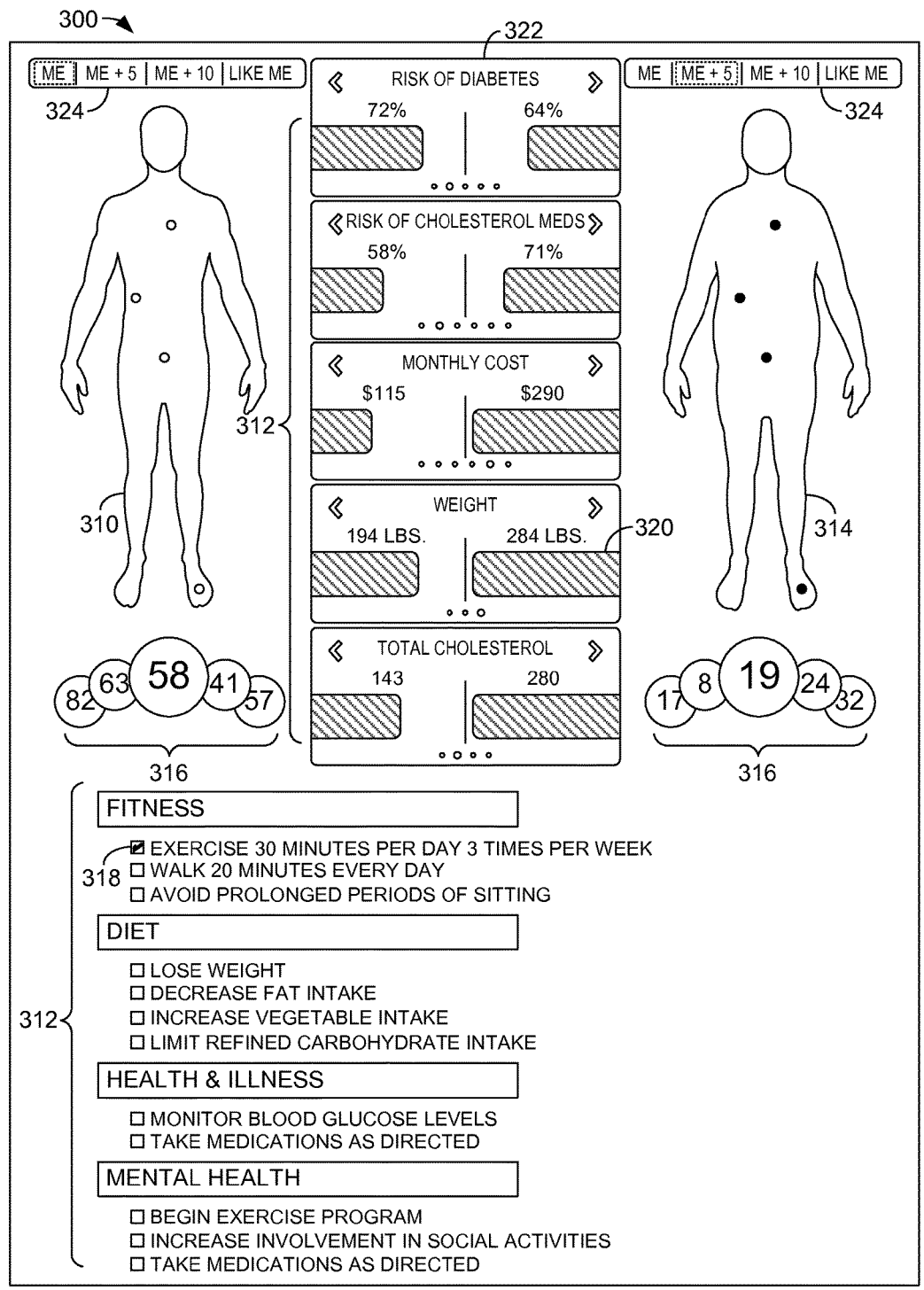
FIG. 3 depicts an exemplary graphical user interface for displaying graphical representations of health-related variables in accordance with an embodiment of the present invention.

Turning now to FIG. 3, an exemplary graphical user interface (GUI) 300 for displaying graphical representations of health-related variables is depicted. The GUI 300 depicts a first display area that is configured to display a first body-image representation 310 of a user at a current period of time. The first body-image representation 310 may be rendered by a rendering component such as the rendering component 222 of FIG. 2. The first body-image representation 310 comprises a graphical representation of actual values of health-related variables associated with the user. As mentioned, the visual appearance of the first body-image representation 310 may be customized by the user in terms of gender, body habitus, skin color, hair color, and the like.

In one aspect of the invention, when the first body-image representation 310 is initially presented to the user, the first body-image representation 310 may graphically display only basic health-related variables related to, for example, demographic data associated with the user (i.e., gender, age, race, etc.). However, as more health-related variables are inputted by the user through, for example, personal health assessments, or become available as the result of biometric screenings, or healthcare visits, the first body-image representation 310 grows in complexity and displays more information.

In another aspect of the invention, if a rendering component determines that there are insufficient health-related variables associated with the user to render an adequate first body-image representation 310, the rendering component may use health-related variables drawn from members of the population-at-large in order to generate the first body-image representation 310. The user may subsequently be presented with a message informing the user of the missing information and the limitations of the health-related variables used to generate the representation 310.

The overall visual appearance of the first body-image representation 310 provides important information to the user. The overall visual appearance includes a general shape of the first body-image representation 310 (thin versus overweight), and/or a colored outline or halo that may indicate certain systemic or multi-organ-system disease conditions. Further, the first body-image representation 310 provides information to the user by utilizing visual indicators to indicate areas of concern; the visual indicators are displayed over an anatomical position that corresponds to an affected organ and/or system. This aspect will be discussed in greater depth below with respect to FIG. 4.

The GUI 300 also comprises a second display area 312 configured to display a variety of health-related variables; the second display area 312 is in the same viewable area as the first display area. The second display area 312 may be rendered by a rendering component such as, for example, the rendering component 222 of FIG. 2. The number and type of health-related variables displayed in the second display area 312 may be configurable by the user and may include variables related to diet, mental health, risk assessment, fitness, medications, financial costs, lifestyle choices, clinical disease states including chronic disease states, and the like. A selectable option may be associated with the health-related variables—for example, a check box. Additionally, user controls, such as slider bars, may be used to modify a health-related variable in the second display area 312. Upon user selection of a health-related variable, or upon modification of a health-related variable, a second body-image representation 314 in a third display area may flex in visual appearance.

By way of illustrative example, suppose the first body-image representation 310 graphically represents health-related variables associated with a user who is overweight and suffers from Diabetes Mellitus Type II (i.e., the representation 310 appears overweight, is outlined with a color indicating Diabetes Mellitus Type II, and has visual indicators located over organs and/or systems affected by Diabetes Mellitus Type II). The user selects a health-related variable 318 under the heading "Fitness." The variable 318 is "Exercise 30 minutes per day 3 times per week." Upon user selection of the variable 318, the second body-image representation 314 changes in visual appearance to reflect weight loss. Additionally, the intensity of the outlining color may be diminished or disappear entirely to indicate that the Diabetes Mellitus Type II has improved or has been cured by the weight loss. As well, the visual indicators change in visual appearance to reflect the positive impact exercise has on organs and/or system affected by Diabetes Mellitus Type II.

Figure 5:
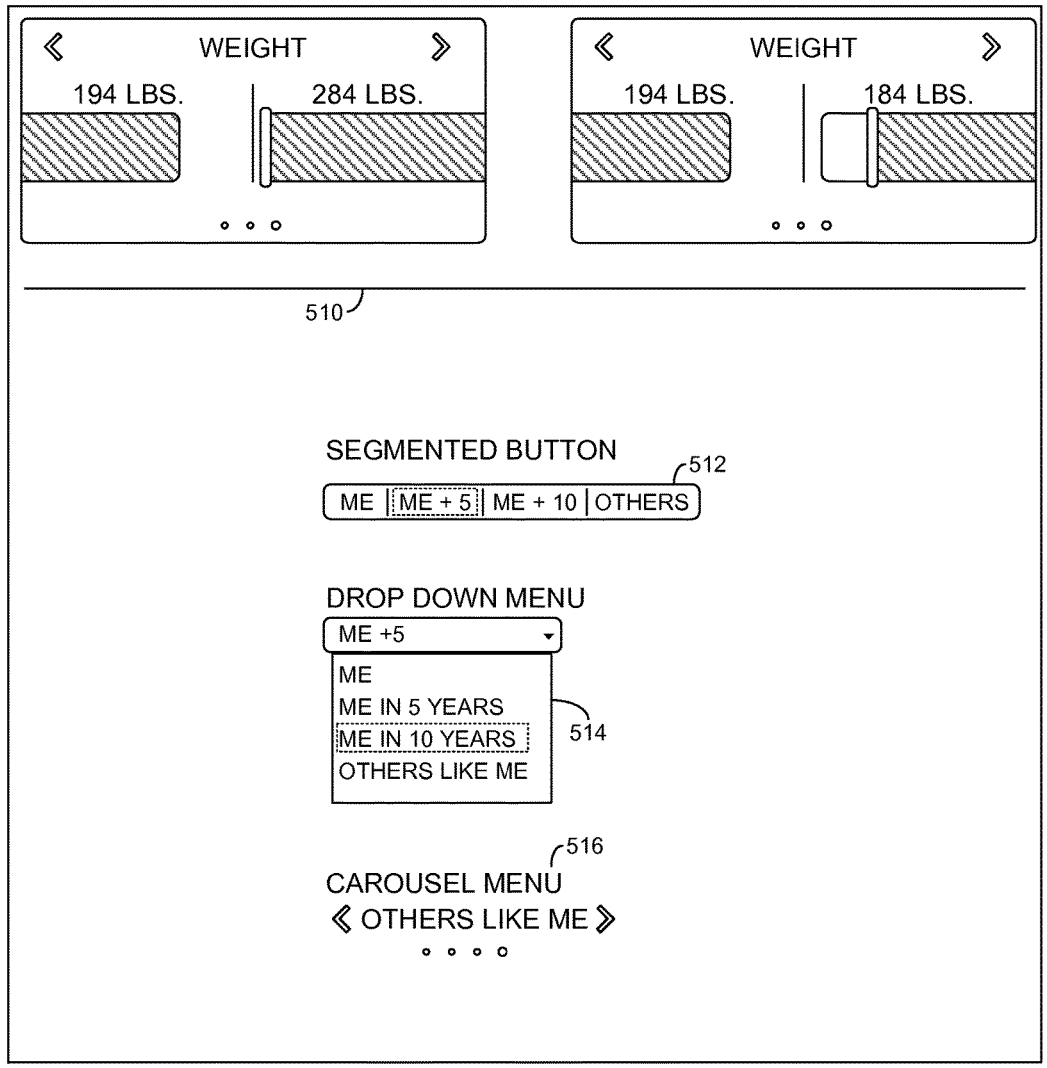
FIG. 5 depicts exemplary selectable controls for modifying health-related variables in accordance with an embodiment of the present invention.

In another illustrative example, suppose the first body-image representation 310 graphically represents health-related variables associated with a user at a certain weight. The user is able to modify, for example, a health-related variable 320 related to weight in the second display area 312. The variable 320 is associated with the second body-image representation 314 which, in turn, represents the user at a future period of time. Upon user modification of the variable 320, the second body-image representation 314 flexes in appearance to reflect the change. In this case, the user may have chosen to increase the weight. Thus, the second body-image representation 314 displays a shape that indicates the increased weight. Additionally, the second body-image representation 314 may be outlined with a certain color to indicate the increased risk of Diabetes Mellitus Type II with the increased weight gain. Additionally, visual indicators may appear that reflect organs and/or systems affected by the weight gain. Element 510 of FIG. 5 illustrates a slidable control that may be used to modify the variable 320.

Turning back to FIG. 3, the second display area 312 is also configured to display risk assessments associated with health-related variables. For example, the health-related variable 322 indicates that the user currently has a 72% risk of developing diabetes based on actual values of health-related variables associated with the user. The variable 322 also indicates a percentile risk (64%) of the user developing diabetes in, for example, five years. The variable 322 may also indicate a percentile risk of developing diabetes for members of the population-at-large that share similar demographic traits with the user. Additionally, the variable 322 may indicate a percentile risk of the user developing diabetes in a clinical "what-if" scenario.

The GUI 300 additionally comprises a third display area illustrating the second body-image representation 314. The third display area is in the same viewable area as the first display area and the second display area 312. The second body-image representation 314 may be a body-image representation of the user at a future period of time, a body-image representation of members of the population-at-large who share similar demographic traits with the user, and/or a body-image representation of the user in a simulated clinical "what-if" scenario. The second body-image representation 314 may be rendered by a rendering component such as the rendering component 222 of FIG. 2.

With respect to the body-image representation of the user at a future period of time, the user may be able to utilize a selectable control to select the period of time. The selectable control is shown by element 324 of FIG. 3. The period of time may be, for example, five years in the future or ten years in the future although other time periods are contemplated to be within the scope of the invention. Elements 512 and 514 of FIG. 5 illustrate exemplary selectable controls that enable the user to select a time period. These controls are only examples, and other types of selectable controls are within the scope of embodiments of the present invention.

Turning back to FIG. 3, in one aspect of the invention, predictive software may be used to personalize the appearance of the second body-image representation 314 at the future period of time. Again, this helps to personalize the graphical display for the user. As mentioned above, the user is able to select or modify one or more health-related variables in the second display area 312 and see their effect on the second body-image representation 314. By displaying the second body-image representation 314 alongside the first body-image representation 310, the user is presented with a powerful visual reminder of the impact that disease conditions and lifestyle choices have on a human body.

In one aspect of the invention, the first body-image representation 310 may represent the user at a future period of time, for example, the user in five years. The second body-image representation 314 may represent the user at a different period of time in the future, for example, the user in ten years. Any and all such variations are within the scope of embodiments of the present invention.

Continuing, the user may make a selection by utilizing element 324 of FIG. 3 (e.g., the "Like Me" selection), such that the second body-image representation 314 represents members of the population-at-large that share similar demographic traits with the user. The comparison of the second body-image representation 314 with the first body-image representation 310 in this instance helps the user to visualize where the user stands in relation to people of similar age, race, and gender. Elements 512, 514, and 516 of FIG. 5 are illustrative examples of the types of selectable controls that enable the user to view a body-image representation that reflects members of the population-at-large.

Turning back to FIG. 3, in one aspect, the first body-image representation 310 may represent members of the population-at large, while the second body-image representation 314 may represent the user at a current period of time, or at a future period of time. Any and all such variations are within the scope of embodiments of the current invention.

Figure 6:
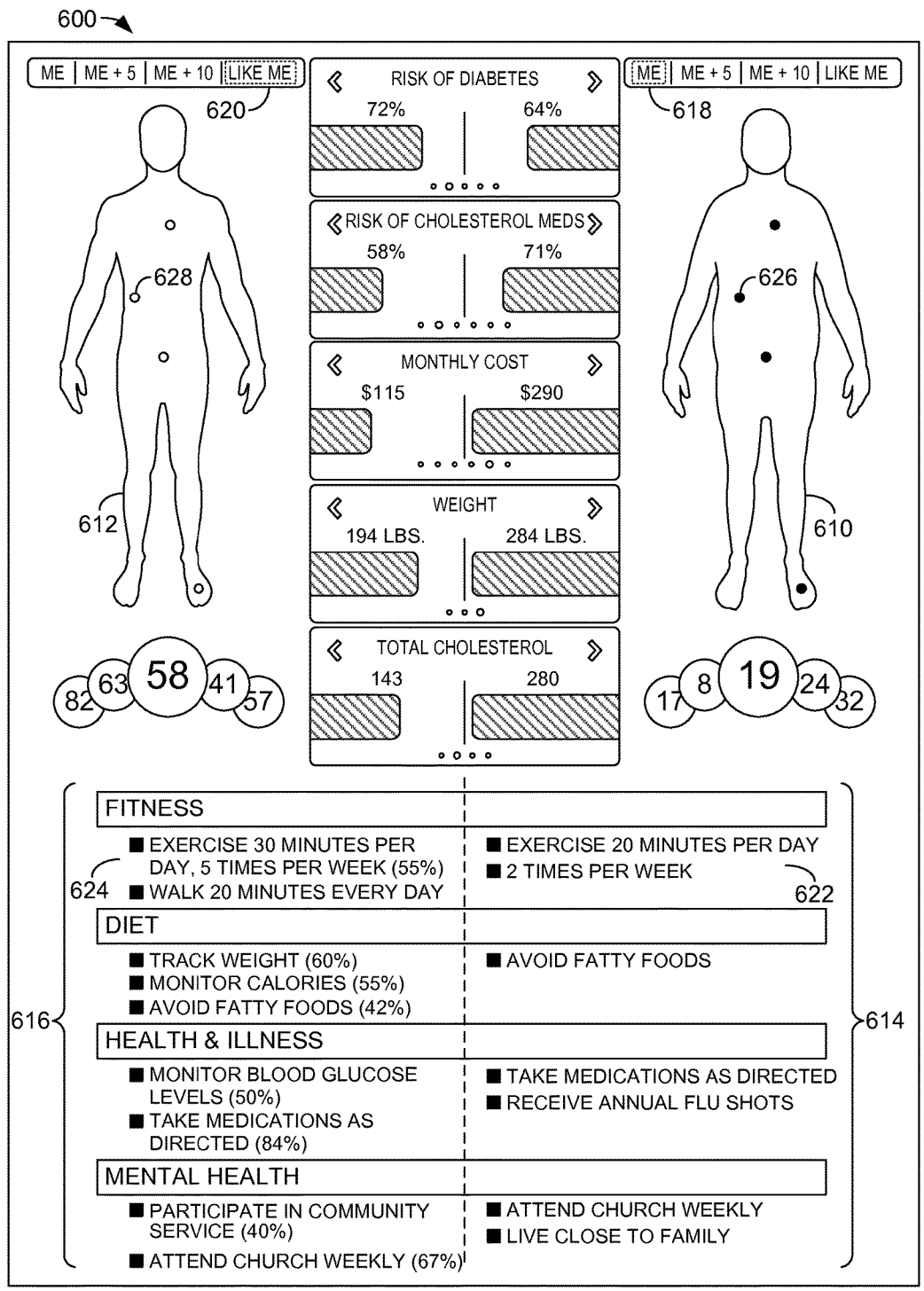
FIG. 6 depicts an exemplary graphical user interface for displaying graphical representations of health-related variables in accordance with an embodiment of the present invention.

FIG. 6 depicts another exemplary graphical user interface (GUI) 600 that may be utilized when comparing a user at a current period of time to members of the population-at-large. GUI 600 depicts a first body-image representation 610 of a user at a current period of time (as shown by the highlighted "Me" element 618), and a second body-image representation 612 of members of the population-at-large who shares similar demographic traits with the user (as show by the highlighted "Like Me" element 620). As seen, the first body-image representation 610 indicates that the user is currently overweight and has a number of different problems areas (as indicated by the solid visual indicators 626). In comparison, the second body-image representation 612 indicates that people who share similar demographic traits with the user are thinner and have less serious problem areas (as indicated by the open visual indicators 628).

Continuing with FIG. 6, the user has made a selection of a number of different health-related variables 614 that represent current health objectives that the user is practicing. Upon user selection of these variables 614, a display of health-related variables 616 is generated; the subject matter of health-related variables 616 generally corresponds to the subject matter of variables 614. The health-related variables 616 represent what different segments of the population-at-large are achieving with respect to the health-related variables selected by the user. For example, the user selects variable 622, "Exercise 20 minutes per day, two times per week," that represents the exercise program currently being utilized by the user. The user is presented with corresponding variables 624 that indicate that 55% of the population that share similar demographic traits with the user exercise 30 minutes per day, 5 times a week, and 70% of the population exercise by walking 20 minutes per day. This type of information enables the user to better gauge what it takes to achieve his or her goals.

Turning back to FIG. 3, the second body-image representation 314 may additionally represent the user in a variety of clinical "what if" scenarios. Upon the selection and/or modification of one or more health-related variables associated with a clinical "what if" scenario and displayed in the second display area 312, the second body-image representation 314 may alter in visual appearance to reflect the influence of the selected variable. Further, the selection and/or modification of a health-related variable may impact how other health-related variables are displayed on the second body-image representation 314. For instance, the selection of a clinical "what if" scenario comprising "decreasing stress levels," may change health-related variables related to mental health and physical health. In turn, the second body-image representation 314 may alter in visual appearance to reflect the changed variables.

The GUI 300 further comprises a fourth display area configured to display one or more health scores 316 associated with the user. The fourth display area is in the same viewable area as the first body-image representation 310, the second display area 312, and the second body-image representation 314. The fourth display area may be rendered by a rendering component such as the rendering component 222 of FIG. 2. The one or more health scores 316 are generated by a computation component using PCA; the computation component may include the computation component 220 of FIG. 2. As mentioned above, a health score is a percentile score between 0 and 100 that gives an indication of the user's overall health or the user's health with respect to one or more discrete health-related variables as compared to members of the population-at-large or a subset of the population-at-large.

In one aspect of the invention, an overall health score 316 is displayed in the fourth display area. On user selection of the overall health score 316, one or more additional sub-health scores 316 may be displayed in the fourth display area. The one or more additional sub-health scores 316 may comprise health scores related to mental health, acute health, injury risk, chronic disease risk, and the like. Health scores 316 associated with a user at a current period of time are determined using actual values of health-related variables. Health scores 316 associated with the user at a future period of time or the user in a clinical "what if" scenario are determined using predicted or expected values of health-related variables. Further, health scores 316 associated with members of the population-at-large are determined using composite values of health-related variables associated with the sample population.

A user's health scores 316 may change in value based upon user selections of, for example, health-related variables and/or clinical "what-if" scenarios in the second display area 312. Further, a user's health scores 316 may also change in value based on user selections of future time periods. When the value of one of the health scores 316 changes, values of other health scores 316 may also change because of the interplay between health-related variables. For example, a decrease in a mental health score (indicating that the user's mental health is not as good as others) may also cause a decrease in a chronic disease risk score. This is because poor mental health may cause chronic conditions to develop or worsen.

Figure 4:
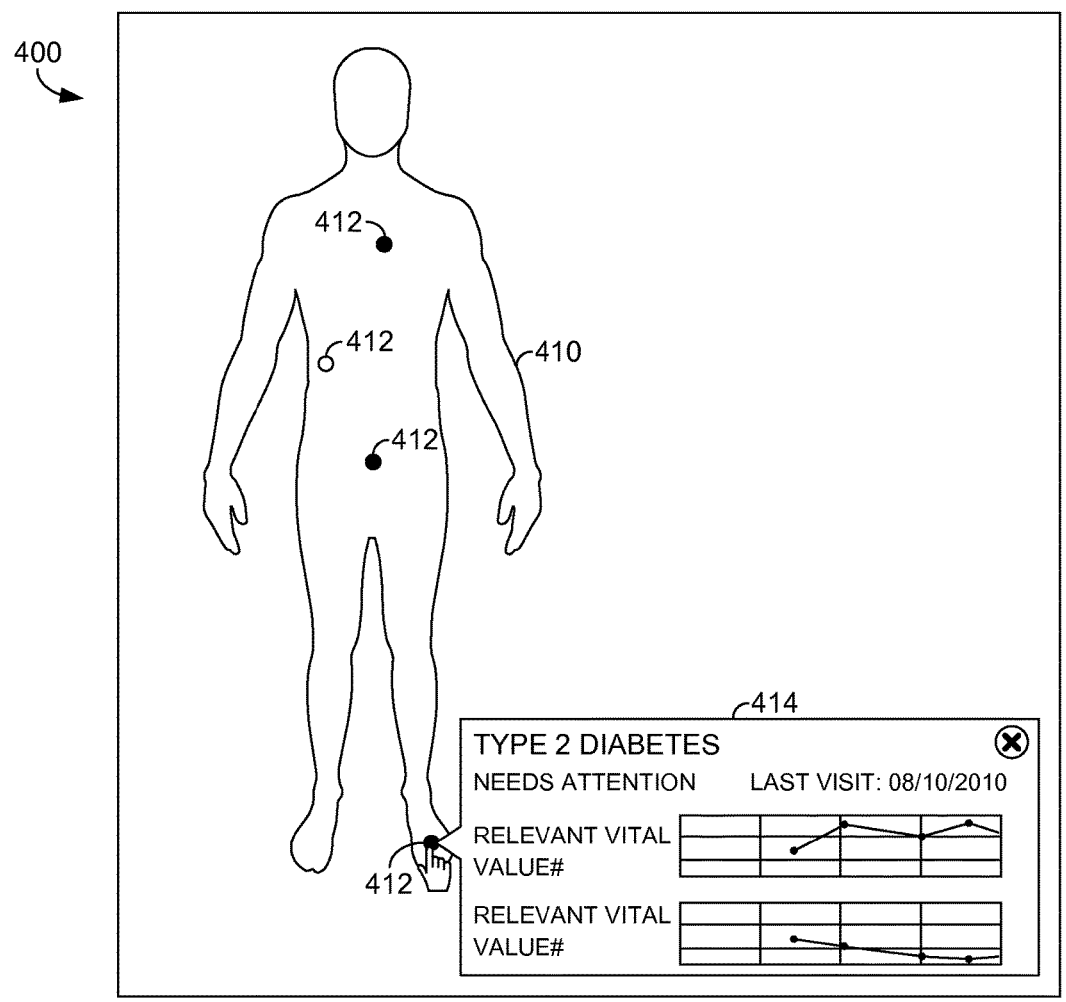
FIG. 4 depicts an exemplary graphical user interface for displaying a detail view of a graphical representation of health-related variables in accordance with an embodiment of the present invention.

Turning now to FIG. 4, an exemplary graphical user interface (GUI) 400 is depicted illustrating a detailed view of a body-image representation 410. The body-image representation 410 comprises one or more visual indicators 412 that are displayed over an anatomical position corresponding to an affected organ and/or system. The visual indicators 412 may comprise dots (open or closed), stylized versions of the affected organ and/or system, or anatomically correct representations of affected organs and/or systems. Further, the visual indicators 412 may be color-coded to indicate a status of the affected organ and/or system. Various colors could be used to indicate, for example, a "critical" status, a "currently managing" status, a "needs attention" status, and an "at risk" status.

The visual indicators 412 on the body-image representation 410 may appear, disappear, or change in color in response to user selections of health-related variables, clinical "what if" scenarios, and/or body-image representations that represent the user at a future period of time, or that represent members of the population-at-large.

The visual indicators 412 are selectable. Upon selection by a user, a detail screen 414 appears that provides more detailed information regarding the selected visual indicator 412. As shown in FIG. 4, such information may include a name associated with the visual indicators 412 (for example, "Type 2 Diabetes"), a status, when the user was last seen by a clinician, and values associated with the visual indicator 412. In one aspect, the detail screen 414 may display images of the affected organ and/or system. For example, if the user is suffering from cirrhosis of the liver, the detail screen 414 may display an image of a cirrhotic liver. Further, the detail screen 414 may display an image of the affected organ and/or system at a future time period, or the detail screen 414 may display an image of an organ and/or system of members of the population-at-large that share similar demographic traits as the user. Any and all such variations are within the scope of embodiments of the present invention.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. One or more non-transitory computer storage media hardware device having computer-executable instructions embodied thereon that, when executed by a computing device having at least one processor, the computing device performs a method of generating graphical representations of health-related variables in the form of body-image representations, the method comprising:

accessing from a data store a plurality of health-related variables associated with a user, wherein the plurality of health-related variables correlate to health issues of the user;

determining, using the at least one processor, a set of health-related variables within the plurality of health-related variables to graphically represent;

transforming the set of health-related variables into a graphical representation; generating a first anatomically correct full-body-image representation of the user, the first anatomically correct full-body-image representation comprising the graphical representation of the set of health-related variables associated with the user at a current period of time;

accessing from the data store composite values of health-related variables associated with members of the population-at-large that share similar demographic traits with the user, the demographic traits comprising age, gender, race, or any combination thereof;

using the composite values of the health-related variables, generating a second anatomically correct full-body-image representation that represents the members of the population-at-large that share similar demographic traits with the user:

transmitting to a user interface of the computing device the first anatomically correct full-body-image representation and the second anatomically correct full-body-image representation, wherein the first anatomically correct full-body-image representation and the second anatomically correct full-body-image representation are presented in the same viewable area on the user interface;

determining a deviation from a comparison between the first anatomically correct full-body image representation and the second anatomically correct fully-body image representation, wherein the deviation identifies and maps to a medical condition of the user; and alerting the user or another of an illness or health concern with a display of the deviation, wherein the deviation is the comparison between the first anatomically correct full-body image representation and the second anatomically correct fully-body image representation.

2. The media of claim 1, wherein a visual appearance of the first full-body-image representation is customizable by the user.

3. The media of claim 2, wherein the user customizes the visual appearance of the full-body-image representation by selecting one or more characteristics, the one or more characteristics including gender, a body habitus, race, and facial characteristics.

4. The media of claim 1, wherein the method further comprises generating and displaying one or more health scores associated with the user in the same viewable area on the user interface as the first and second anatomically correct full-body-image representations.

5. The media of claim 1, wherein the health-related variables include variables related to diet, a health score, mental health, fitness, medications, financial costs associated with healthcare, and clinical disease states.

6. The media of claim 1, wherein the health-related variables are derived from a user-supplied personal health assessment, biometric screenings, and health-related insurance claims.

7. The media of claim 1, wherein the first full-body-image representation is configured to adaptively alter in appearance in response to a user selection of one or more health-related variables.

8. The media of claim 1, further comprising:
one or more visual indicators displayed on at least the first full-body-image representation or the second full-body-image representation, the one or more visual indicators indicating areas of concern for the user.

9. The media of claim 8, wherein the one or more visual indicators are displayed over an anatomical position of an affected organ or system.

10. The media of claim 9, wherein the one or more visual indicators are color-coded to indicate a status of the affected organ or system.

11. The media of claim 9, wherein the one or more visual indicators are selectable by the user, and wherein selection of the one or more visual indicators displays additional information about the visual indicator.

12. One or more non-transitory computer storage hardware device, having computer-executable instructions embodied thereon that, when executed by a computing device having at least one processor, the computing device performs a method of generating graphical representations of health-related variables in the form of body-image representations, method comprising:

accessing from a data store a plurality of health-related variables associated with a user, wherein the plurality of health-related variables correlate to health issues;

determining, using the at least one processor, a set of health-related variables within the plurality of health-related variables to graphically represent;

transforming the set of health-related variables into a graphical representation;

generating a first anatomically correct full-body-image representation, the first anatomically correct full-body-image representation comprising the graphical representation of health-related variables associated with the user at a current period of time;

generating a second anatomically correct full-body-image representation, the second anatomically correct full-body-image representation comprising a graphical representation of health-related variables associated with the user at a future period of time, wherein the second anatomically correct full-body-image representation is located in the same viewable area as the first anatomically correct full-body-image representation;

comparing the first anatomically correct full-body-image representation and second anatomically correct full-body-image representation; and alerting the user or another of an illness or health concern with a display of the comparison of the first anatomically correct full-body image representation and the second anatomically correct fully-body image representation.

13. The media of claim 12, wherein the second full-body-image representation adaptively alters in visual appearance in response to a selection by the user of at least one health-related variable of a set of health-related variables.

14. The media of claim 13, wherein the user selects the at least one health-related variable by at least one of manipulating a slider control or checking a box associated with the at least one health-related variable.

15. The media of claim 13, wherein the user selection of the at least one health-related variable automatically causes other health-related variables within the set of health-related variables to adjust accordingly.

16. The media of claim 12, wherein the graphical representation of health-related variables associated with the user at a future period of time comprises:
(1) a graphical representation of health-related variables at a period of time five years from the current period of time, or
(2) a graphical representation of health-related variables at a period of time ten years from the current period of time.

17. A computerized method carried out by at least one server having at least one processor for displaying graphical representations of health related variables in the form of body-image representations, the method comprising:

accessing from a data store a plurality of health-related variables associated with a user, wherein the plurality of health-related variables correlate to health issues;

determining, using the at least one processor, a set of a health-related variables within the plurality of health-related variables to graphically represent;

transforming the set of health-related variables into a graphical representation;

generating a first display area configured to display a first anatomically correct full-body-image representation of the user;

displaying the first anatomically correct full-body-image representation of the user in the first display area, the first anatomically correct full-body-image representation comprising the graphical representation of a set of health-related variables associated with the user at a current period of time;

generating a second display area configured to display at least a portion of the set of health-related variables;

displaying the at least a portion of the set of health-related variables in the second display area, the second display area located in the same viewable area as the first display area, the at least a portion of the set of health-related variables having a selectable option associated therewith;

generating a third display area configured to display a second anatomically correct full-body-image representation of a user;

displaying the second anatomically correct full-body-image representation of the user in the third display area, the third display area located in the same viewable area as the first display area and the second display area, the second anatomically correct full-body-image representation comprising a graphical representation of health-related variables associated with the user at a future point in time; and generating a fourth display area configured to display one or more health scores associated with the user;

displaying the one or more health scores associated with the user in the fourth display area, the fourth display area located in the same viewable area as the first, second, and third display areas; and alerting the user or another of an illness or health concern with the display of the first anatomically correct full-body-image representation, the at least a portion of the set of health-related variables, the second anatomically correct full-body-image representation, and the one or more health scores.

18. The method of claim 17, wherein the one or more health scores comprise an overall health score and one or more sub-health scores, and wherein the one or more health scores comprise a percentile score bounded between zero and 100 and indicating a numerical representation of the user compared to members of the population-at-large.

19. The method of claim 18, wherein the one or more sub-health scores include a mental health score, an acute health score, an injury score, and a chronic disease score.

20. The method of claim 17, further comprising generating one or more visual indicators associated with a health status and displaying the visual indicators over an anatomical position of a corresponding affected organ and/or system of the body.

* * * * *